US008114022B2

(12) United States Patent
Crowther et al.

(10) Patent No.: US 8,114,022 B2
(45) Date of Patent: *Feb. 14, 2012

(54) BUSINESS METHOD FOR GENERATING ADVERTISING CLAIMS

(75) Inventors: Jonathan Mark Crowther, Egham (GB); Anke Sieg, Englefield (GB); Paul Jonathan Matts, Addlestone (GB); Peter Blenkiron, Egham (GB)

(73) Assignee: The Procter & Gamble Company, Cincinnati, OH (US)

( * ) Notice: Subject to any disclaimer, the term of this patent is extended or adjusted under 35 U.S.C. 154(b) by 1566 days.

This patent is subject to a terminal disclaimer.

(21) Appl. No.: 11/449,937

(22) Filed: Jun. 9, 2006

(65) Prior Publication Data

US 2007/0050202 A1 Mar. 1, 2007

(30) Foreign Application Priority Data

Aug. 31, 2005 (EP) .................................... 05018928

(51) Int. Cl.
*A61B 5/00* (2006.01)
*A61B 6/00* (2006.01)
(52) U.S. Cl. ......................... 600/306; 600/473; 600/587
(58) Field of Classification Search .................. 600/300, 600/306, 473–480, 587
See application file for complete search history.

(56) References Cited

U.S. PATENT DOCUMENTS 6,069,689 A 5/2000 Zeng
2004/0185430 A1 9/2004 Lefebvre

FOREIGN PATENT DOCUMENTS

EP 1314395 A2 * 11/2002
EP 1 314 395 A2 5/2003

OTHER PUBLICATIONS

Peter J Caspers, Gerald W Lucassen, Elizabeth A carter, Hajo A Bruining and Gerwin J Puppels, In Vovo Confocal Raman Microspectroscopy of the skin: Noninvasive Determination of Molecular Concentration Profiles, Journal of Investigative Dermatology, (2001), 116, 434-442.*
U.S. Appl. No. 11/510,898 (P&G Case CM3012), filed Aug. 28, 2006; Office Actions and Responses from Mar. 1, 2007 to Oct. 5, 2010.
U.S. Appl. No. 12/961,589 (P&G Case CM3012D), filed Dec. 7, 2010; Office Actions and Responses from Dec. 27, 2010 to Apr. 7, 2011.
PCT International Search Report Dated Feb. 6, 2007, 42 pages.
Automated depth-scanning Confocal Raman microspectrometer for rapid in vivo determination of water concentration of water concentration profile in human skin; P.J. Caspers, G.W. Lucassen, H.A. Bruining and G. J. Puppels; J. Raman Spectrosc. 31, 813-818 (2000).
In vivo Confocal Raman Microspectroscopy of the Skin: Noninvasive Determination of Molecular Concentration Profiles, P.J. Caspers, G.W. Lucassen, E. A. Carter, H.A. Bruining and G. J. Puppels, The Journal of Investigative Dermatology, vol. 133, No. 3 Mar. 2001, 434-442.
Confocal Raman Microscopy for Cosmetic Applications, published in "Raman Update", a publication by Horiba Jobin Yvon, Winter Edition 2005.
Confocal Raman Microspectroscopy—Measuring the Effects of Topical Moisturisers on Stratum Corneum Water Gradient In Vivo; Anke Sieg, Jonathan Crowther, Peter Blenkiroa, Curtis Marcott, Paul J. Matts; Procter & Gamble Technical Centres Ltd., Rusham Park Technical Centre, Whitehall Lane, Egham, Surrey, UK, TW20 9NW; The Procter & Gamble Company, Miami Valley Innovation Center, Cincinnati, USA, OH 45252-8707, Jan. 21, 2006.
In Vivo Chemical Investigation of Human Skin Using A Confocal Raman Fiber Optic Microprobe; L. Chrit, C.Hadjur, S. Morel, G. Sockalingum, G. Lebourdon, F. Leroy, M. Manfait; Journal of Biomedial Optics; Jul./Aug. 2005, vol. 10(4), 1-11.
In Vitro and In Vivo Raman Spectroscopy of Human Skin, P.J. Caspers, G.W. Lucassen, R. Wolthuis, H.A. Bruining and G. J. Puppels, Biospectroscopy, vol. 4, 1998, S31-S39.
In Vivo Raman Spectroscopy, Gerwin J. Puppels, Tom C. Bakker Schut, Peter J. Caspers, Rolf Wolthuis, M. van Aken, A. van der Laarse, and Hajo A. Bruining, Handbook of Raman Spectroscopy, Practical Spectroscopy Series vol. 28 supplied by The British Library, 549-574, Jul. 1, 2003.
In Vivo Near-infrared Spectrometry, Claudia E. W. Gributs and David H. Burns, Handbook of Vibrational Spectroscopy, vol. 5, 3362-3375, 2002.
"Combined In Vivo Confocal Raman Spectroscopy and Confocal Microscopy of Human Skin", P.J. Caspers, G.W. Lucassen and G.J. Puppels, *Biophysical Journal*, vol. 85, Jul. 2003, 572-580.
"Stratum Corneum Swelling. Biophysical and Computer Assisted Quantitative Assessments", Lars Norlén, Axel Emilson, Bo Forslind, *Archives of Dermatological Research*, vol. 289 1997, 506-513.

* cited by examiner

*Primary Examiner* — Michael G Hartley
*Assistant Examiner* — Jagadishwar Samala
(74) *Attorney, Agent, or Firm* — John G. Powell; Megan C. Hymore

(57) ABSTRACT

Business method for generating advertising claims by utilizing Confocal Raman Spectroscopy (CRS) for dermatological studies. The methods of the invention can be carried in vitro (either artificial skin or a sample of skin) or in vivo (directly on the human skin of a person).

14 Claims, 4 Drawing Sheets

BUSINESS METHOD FOR GENERATING ADVERTISING CLAIMS

FIELD OF THE INVENTION

The present invention relates to a business method for generating advertising claims. The business method utilizes Confocal Raman Spectroscopy (CRS) for dermatological studies. In particular, the invention relates to a business method for generating advertising claims by: 1) determining the thickness of the Stratum Corneum (SC) on a test area of the skin before use of a personal care product; 2) use of the personal care product; and 3) determining the thickness of the SC after use of the personal care product. The measurement technique is unique in being able to measure both skin thickness and the distribution of water and/or actives in the skin. The methods of the invention can be carried out in vitro (either artificial skin or a sample of skin) or in vivo (directly on the human skin of a person). The in vivo method has the ability to make in vivo measurements quickly enough to provide useful data on live subjects, without being affected by subjects moving during data acquisition or having to use a laser power so high that the skin is burned.

BACKGROUND OF THE INVENTION

Skin is composed of two main layers, the dermis and epidermis, which are in turn composed of sub-layers. The surface of the skin is the outermost layer of the epidermis and is called the Stratum Corneum (SC). It is composed mainly of dead cells that lack nuclei and contain keratin, a protein that helps keep the skin hydrated by preventing water evaporation. In addition, these cells can also absorb water.

The standard method for measuring skin hydration in the SC is to measure a change in the electrical properties of the skin (specifically the capacitance), which is related to the degree of hydration. The apparatus commonly used for this measurement is called a Corneometer® (available from Courage & Khazaka).

The present invention generates advertising claims by using a different technique to measure skin moisturization, based on Confocal Raman Spectroscopy. Raman spectroscopy is the measurement of the wavelength and intensity of inelastically scattered light from molecules. Raman scattered light occurs at wavelengths that are shifted from the incident light by the energies of molecular vibrations. The mechanism of Raman scattering is different from that of infrared absorption, and Raman and IR spectra provide complementary information. For further background information on Raman spectroscopy, see for example "Fundamentals of Molecular Spectroscopy", C. N. Banwell, McGraw Hill, 1983.

Raman spectroscopy is an improvement over the standard method Corneometry, as it provides quantitative interval data on the water distribution within the skin. While the corneometer is non-quantitative and provides only a single number, Raman spectroscopy gives % hydration readings at specific depths within the SC, allowing a water profile to be built. Previously, this type of information would have only been available through taking a skin biopsy, which is painful and not ideal for a clinical type study, where perhaps multiple products and timepoints are being investigated.

SUMMARY OF THE INVENTION

One aspect of the invention is a business method for generating advertising claims, the method comprising the steps of:

(a) determining the before use thickness of the Stratum Corneum on an area of a test subject's skin comprising the steps of:
  i. measuring the concentration profile of a Raman-active material as a function of depth within the test area using Confocal Raman Spectroscopy; then
  ii. processing the Confocal Raman Spectroscopy data obtained to determine said before use thickness of the Stratum Corneum;

(b) providing said test subject with a personal care composition and instructions for use of said personal care composition;

(c) determining the after use thickness of the Stratum Corneum on an area of a test subject's skin after the use of said personal care composition comprising the steps of:
  i. measuring the concentration profile of a Raman-active material as a function of depth within the test area using Confocal Raman Spectroscopy; then
  ii. processing the Confocal Raman Spectroscopy data obtained to determine said after use thickness of the Stratum Corneum;

(d) utilizing said before use thickness and said after use thickness to generate said advertising claims.

DETAILED DESCRIPTION OF THE INVENTION

Figure 1:
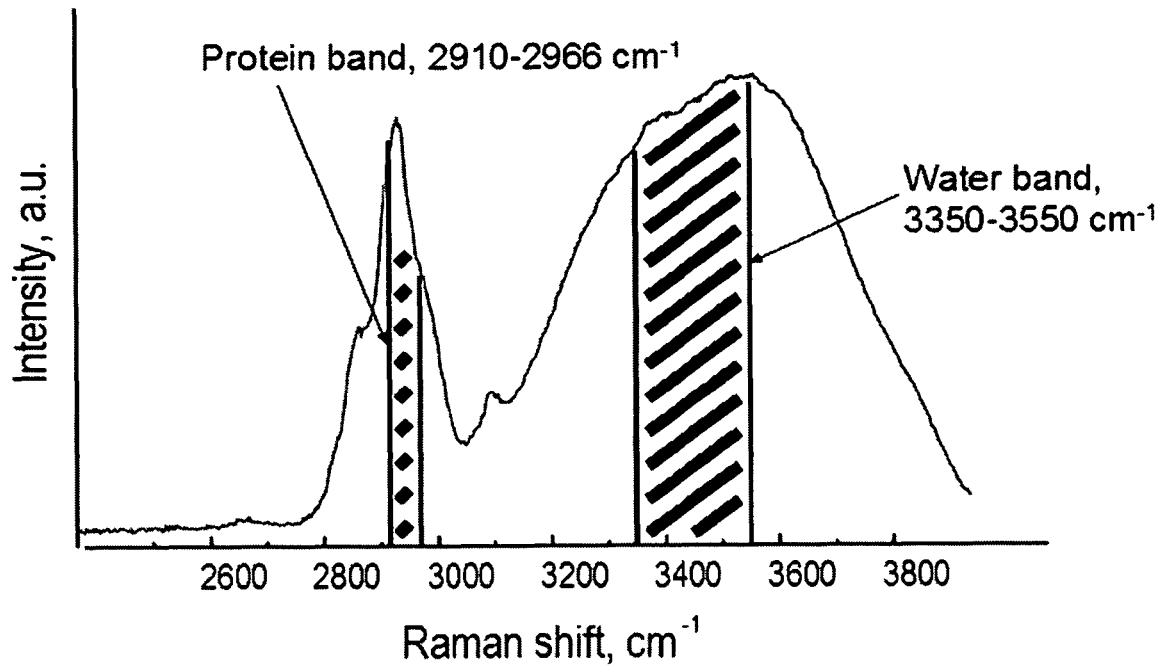
FIG. 1 shows a typical high wavenumber spectrum of hydrated skin and the relevant areas measured when determining the % hydration level.

The present invention is directed to a business method for generating advertising claims. The business method comprises the steps of: 1) determining the before use thickness of the Stratum Corneum (SC) on an area of a test subject's skin by measuring the concentration profile of a Raman-active material as a function of depth within the test area using Confocal Raman Spectroscopy, then processing the data obtained to determine the before use thickness of the SC; 2) providing the test subject with a personal care composition and instructions for use of the personal care composition; 3) determining the after use thickness of the SC on an area of a test subject's skin after the use of the personal care composition by measuring the concentration profile of a Raman-active material as a function of depth within the test area using Confocal Raman Spectroscopy, then processing the data obtained to determine the after use thickness of the SC; and utilizing the before use thickness and the after use thickness to generate the advertising claims. The method may be utilized in locations including, but not limited to, stores (specialty shops, mass stores, etc.), doctor's office, spas, etc. The method of the present invention may generate advertising claims in the form of before use and after use advertising claims.

A. Determining Thickness of the Stratum Cornuem

1. Confocal Raman Spectroscopy

The thickness of the Stratum Cornuem (SC) may be determined using Confocal Raman Spectroscopy (CRS). The method of CRS described herein is used to determine both the before use thickness and the after use thickness in generating advertising claims.

CRS uses a microscope system to focus laser light to a point. The light at the point of focus is of high intensity which is where the Raman signal is generated from. Measurements as a function of depth are carried out by moving the microscope objective lens so that it focuses the light at specific locations within the substrate of interest (e.g. the SC). It is possible to analyze any material as long as it is transparent enough to allow sufficient light to enter and leave from the depth of interest and it has a unique Raman spectra. By moving the objective lens in small increments, a profile of Raman spectra as a function of depth of the SC can be produced. The Raman spectra contain peaks corresponding to the different functional groups of the chemicals present within the sample. The locations of these peaks are determined by the precise chemical structure of the components. Once the peak locations for different components of the sample are known, ratioing of one component to the others present can be carried out. For instance, % water in skin can be calculated by ratioing the amount of water and protein as calculated from the areas under the curves in the part of the spectra corresponding to water and protein respectively, and applying a proportionality constant (as detailed below).

Any suitable commercially available CRS equipment can be used. One example is a River Diagnostics Model 3510 Confocal Raman Microspectroscopy system (software version—RiverIcon v.1). This has been designed for use as an in-vivo, non invasive skin analysis device, enabling qualitative and semi-quantitative analysis of molecular concentrations and concentration profiles within the skin. The system incorporates a CCD detector combined with a microscope objective lens to enable focusing of the laser light into the skin and collection of the returning signal. Two (2) lasers are used—a 671 nm red laser for water profiling (operating in the high wavenumber region from 2500-4000 $cm^{-1}$), and a 785 nm near IR laser for low wavenumber fingerprint region (natural moisturizing factor (NMF) and other active ingredients measurement). The peaks for the natural moisturizing factors are present in the low wavenumber fingerprint region which is the region about which this laser gives information. Therefore, by measuring the fingerprint region, information about the natural moisturizing factors can be determined. Profiles in the high wavenumber region may be measured using 1s acquisition times per spectra, and in the fingerprint region using 10s acquisitions per spectra. Typically 2 or 3 µm spacings between spectra may be used. The top few hundred microns of the skin are transparent to the light from both the 671 nm and 785 nm lasers allowing profiling within the SC using this arrangement.

The points forming the hydration profile as a function of depth within the SC are derived by the software using the Raman spectra acquired for each depth value. The software may use the calculation method as outlined in Peter Caspers' Ph.D. Thesis ('In-vivo skin characterization by confocal Raman spectroscopy', 2003, Erasmus University, Rotterdam, the Netherlands). For example, as explained in this thesis, the area between 3350-3550 $cm^{-1}$ may be integrated for the water band [water], and 2910-2966 $cm^{-1}$ for the protein band [protein] (a sample spectra showing the areas measured for water and protein is given in FIG. 1).

The percentage hydration may then be calculated for each depth with this formula:

$$\% \text{ hydration} = [\text{water}]/([\text{water}] + r.[\text{protein}])$$

wherein r is a proportionality constant (derivation of the proportionality constant is described in the Peter Caspers' Ph.D. thesis noted above).

Figure 2:
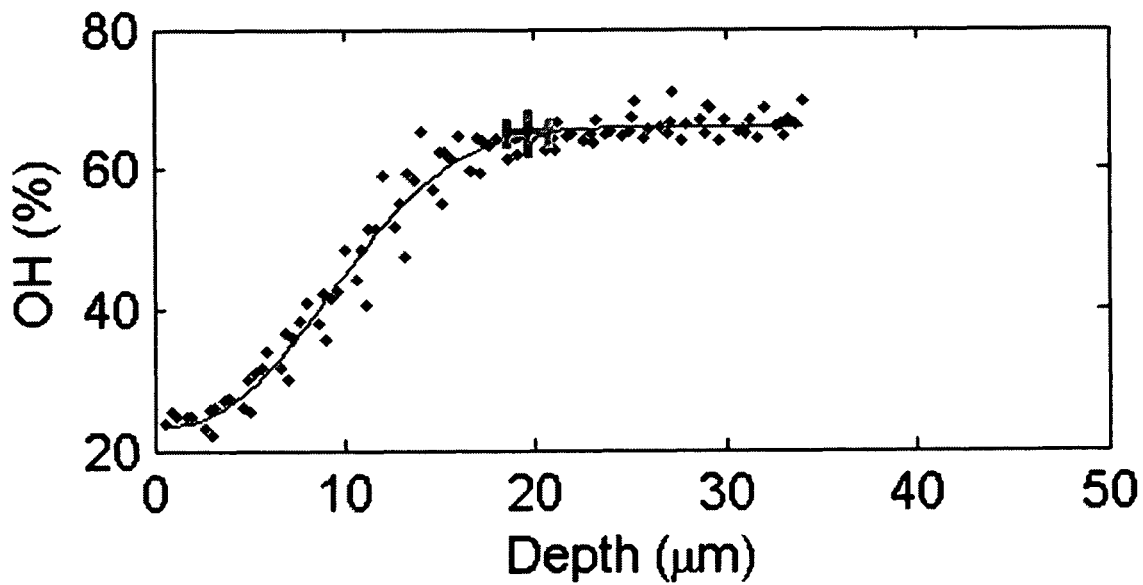
FIG. 2 shows a typical Confocal Raman Spectroscopy profile of the water content of skin as a function of depth. In this example, a typical water profile showing the surface of the Stratum Corneum (SC) at depth=0 with 20-30% hydration, rising to the 60-70% hydration within the body at a depth of approximately 20 μm for forearm skin. The line of best fit through the data points has been fit using a Weibull growth curve model.

The procedure to determine percentage hydration is carried out automatically at each point of the spectra by the associated RiverIcon software and results in the formation of a hydration profile (see FIG. 2). A similar process may be followed when looking at different active species (for example vitamins, and amino acids), where a principal component analysis using well defined peak locations is used to calculate a profile for each of the ingredients of interest. Again, this is carried out within the standard software provided with the equipment, and the data are outputted in the form of a profile for the ingredient of interest as a function of depth.

In principle, anything which is Raman-active can be measured within the skin using this technique. For a specific vibrational mode to be Raman-active, there must be a change in the polarizability of the molecule caused by the vibration. It has already been shown in the literature that water and the amino acids which make up natural moisturizing factors (NMF) can be analyzed within the skin, along with cholesterol, lactic acid, and keratin. Due to the complex structure of most ingredients of interest within skin care formulations, there will normally be some vibrations associated with any given molecule of interest which will be Raman-active. In order for the molecules of interest to be measured in a Raman profile they must fulfill two criteria: 1) they must have peaks which are sufficiently distinct from other components within the skin, and 2) the ingredient must be present in sufficient quantity to be detected. The absolute intensity of the peaks in a spectrum will be determined by how strong the change in polarizability is and will vary from compound to compound. Peak location within the spectrum is determined by the functional groups present within the molecule.

2. Processing Data

The method of data processing described herein is used to determine both the before use thickness and the after use thickness in generating advertising claims. The data points gathered are processed to be more readily usable. Data points that make up each profile may be saved as a tab delimited text file and imported into a suitable mathematical software, for example Matlab. In the exemplary system used, up to 8 profiles for any given site may be imported. The dataset (containing all profiles) may then be treated as a cloud of points through which a line of best fit is put. The mathematical model for the line of best fit may be based on the Weibull model, although different models may be used (e.g. polynomial regression).

The Weibull distribution is widely used in reliability and life (failure rate) data analysis and as a biological growth model. The equation for the Weibull model used here is given below.

$$y = a - (a-b) * \exp(-(x/c)^d)$$

Where a, b, c and d are variables determined during the optimization of the line of best fit by the mathematical software. A line of best fit based upon this model is fitted to the dataset (see FIG. 2), and using this equation different parameters of the skin can be determined (for example, bottom of the SC, complete area under the curve from the surface to the base of the SC).

During the calculation of the line of best fit through the dataset, the determination of the leveling off point of the curve is also carried out. The leveling off point is determined using a gradient threshold on the Weibull model. A value for the gradient threshold may be set by the operator during data analysis. The leveling off point is taken where the slope on the modeled curve matches the threshold set. This leveling off point corresponds to where the water rich living tissue of the epidermis meets the SC, e.g. the bottom of the SC.

When analyzing an entire study, a subset of the data is chosen at random and analyzed using different gradient threshold values. The operator then determines the most accurate fit for the leveling off point and uses the corresponding gradient threshold value for analysis of the entire study. As discussed above, the operator makes this assessment by first looking for where the curve leveled off. This is done by eye, setting different gradients into the software and seeing the location of the resulting leveling off points. Additionally, the operator may choose to run fingerprint profiles on a few locations at exactly the same points as the hydration profiles. This allows one to see the presence of NMF, which only starts to be expressed at the bottom of the SC. Typically, the location where the NMF starts to be seen corresponds to where the operator finds the most accurate fit for the leveling off point in the hydration profiles. Importantly, once a value is set for a given study, that value is then applied to the entire dataset.

The need for operator choice for the gradient threshold arises from a number of factors. For example, the skin on different body parts has inherently different water profiles. Also, the skin's natural hydration state is strongly influenced by the time of year and associated weather conditions. It should be emphasized that once a value for the gradient threshold has been derived for the small subset of data from the entire study, that value is normally used for the entire analysis. Typical values for the gradient threshold on volar forearm skin are between 0.4 and 1.0, and this range may be used as a starting point when determining the appropriate value. An example data set fitted with the Weibull model is shown in FIG. 2. It is also possible to use other mathematical operations to determine the leveling off point, such as the point at which the % hydration reaches a fixed percentage of the upper asymptote of the Weibull model. As with the use of the gradient threshold, this provides a route to determining the location of the bottom of the SC.

B. Personal Care Composition

The term "personal care composition," as used herein, refers to a product that is intended to have an effect on skin. The term includes cosmetic products, whose purpose is to improve the appearance of skin, as well as therapeutic treatments, whose purpose is to prevent or treat a skin disease (these terms are not mutually exclusive). Also included are products which are not directly applied on the skin, e.g. nutraceuticals which are ingested by the user. The personal care composition of the present invention may be a skin care composition. The skin care composition may include moisturizing agents. Non-limiting examples of skin-care compositions include leave-on products (e.g. moisturizing creams, self-tanning products, tinted moisturizers, powders, foundations, conditioning wipes, etc.) and rinse-off products (shower gels, in-shower moisturizers, foaming wipes, etc.).

C. Use of Data to Generate Advertising Claims

The advertising claims may be determined based on the before use thickness and after thickness. The before use and after use thickness indicate the effectiveness of a personal care composition. The effectiveness of a personal care composition is normally expressed as the change of a certain skin quality between the beginning and the end of the study. Confocal Raman Spectroscopy may be used to quantify the change of concentration of a Raman-active material within the skin. Therefore, it may be used to determine the effectiveness of a personal care composition when a Raman-active material can be linked the effect of the composition studied. For example, a change in skin hydration, which can be linked to the concentration of water within the skin, can be measured using the CRS technique because water is a Raman-active material. Similarly, any Raman-active materials that can be linked to the effectiveness of a personal care composition (e.g. including, but not limited to, niacinamide, water, natural moisturizing factors (NMF), vitamins, cholesterol, ceramides, urea, urocanic acid, glycerin, amino acids, etc.) may also be used to quantify its effectiveness.

For effectively quantifying the effectiveness of a personal care composition using Confocal Raman Spectroscopy, it is important to take into account the change of thickness of the SC during the study. Without wishing to being bound by theory, this may be because changes in the hydration state of the skin alter its thickness, or that certain skin actives (e.g. including, but not limited to, niacinamide, water, natural moisturizing factors (NMF), vitamins, cholesterol, ceramides, urea, urocanic acid, glycerin, amino acids, etc.) may increase skin cells proliferation. Therefore, it may not be appropriate to compare values obtained at the beginning and the end of the study at a constant depth (e.g. 10 μm). Constant depth refers to an absolute distance from the surface of the SC, for example 10 um above. This is distinguishable from relative depth (e.g. half way through the SC), where thickness changes within the SC over the course of the treatment is taken into account. Using this technique to derive information about changes in SC thickness from the shape of the profile enables one to determine relative depths.

For actives delivered from the composition, it is normally important to know depth of penetration and % concentration as a function of depth. As such, it is important to reference any change in the quantity of a Raman-active material % hydration changes to % depth. Also, as the thickness of the SC may have changed, the parameter of total area under the curve from the surface to the bottom of the SC becomes important as a total hydration measure. Wrongly considering the SC to be fixed in thickness throughout the study may lead to an incorrect interpretation of the data.

The thickness of the SC at the beginning and then at the end of the study may be determined using the method described above which employs a CRS technique. Measuring the water concentration profile using CRS and processing the data obtained is a good way to determine SC thickness. If the effect to be measured is skin hydration, then only one measure of the concentration profile at the beginning and at the end of the study needs to be performed, because the data generated for determining the SC thickness can also be used to determine the water content of the SC.

There are different ways to express the effectiveness of a personal care composition using the data generated by CRS and the SC thickness, of which two preferred examples are outlined here.

First, a specific relative depth of the SC (e.g. half-way) may be selected, and the amounts of Raman-active material (e.g. water) linked to the effect of the personal care composition (e.g. skin hydration) to be determined at this relative depth at the beginning and at the end of the study may be compared.

An alternative way to express the effectiveness of the composition is to measure the area under the curve (integrating) between the skin surface and the end of SC (e.g. as determined by CRS, as described above). Dividing the value obtained for the surface area at the end of the treatment by the value obtained for the surface area at the beginning of the treatment gives a measure of the effectiveness of the composition in % of increase. This is a measure of increase in the total amount of ingredient X (e.g. water for hydration measurements) within the SC. For example, if the area under the curve at the start of the experiment is 1000 and the area after using the product is 1100, the total water holding capacity of the SC has increased by 10%. This method of quantifying the effect also works well for quantifying skin hydration. Also, the total area under the curve for individual NMF's could be linked to health of the skin (as NMF's are beneficial to the water holding capability of the SC and are readily washed out).

EXAMPLE 1

Figure 3:
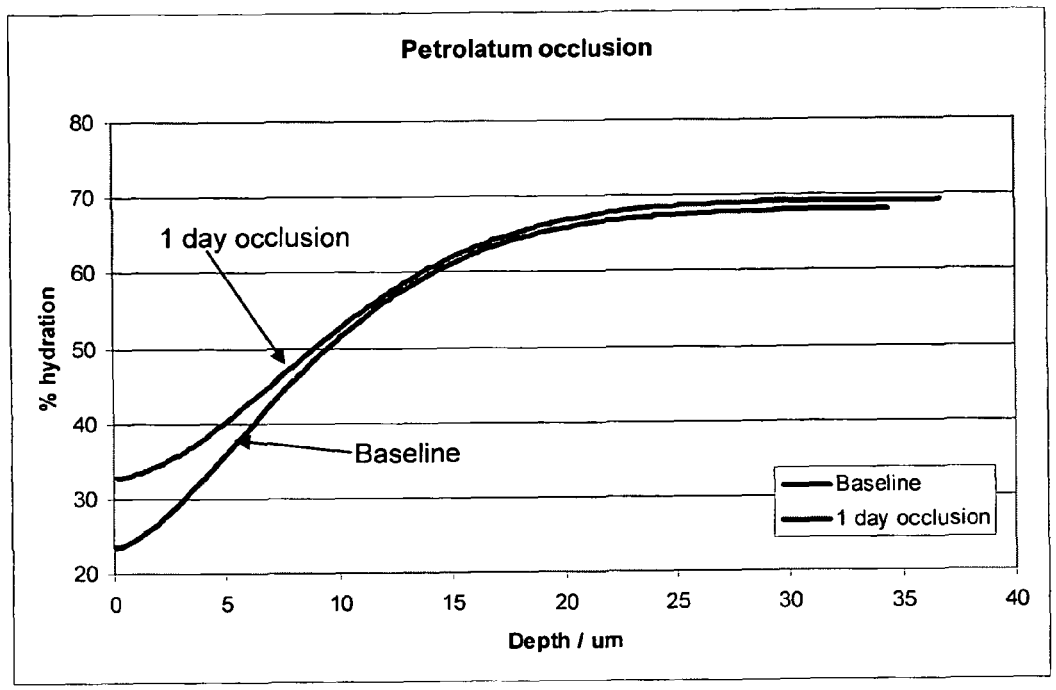
FIG. 3 shows the hydration profile before and after application of petrolatum.

Single Variable Analysis of Hydration Levels within the Skin—Petrolatum Occlusion To demonstrate the effects of a single variable on skin hydration, a set of baseline spectra is recorded (the site to be used is dry wiped to remove surface sebum before the measurements are taken via CRS to provide a benchmark for the state of the individual's SC before treatment). Petrolatum is then applied to the same area of the forearm 4 times over a 24 hour period with the aim of promoting skin hydration via occlusion. After 24 hours, the site is dry wiped to remove any surface contamination and a further set of profiles collected via CRS (FIG. 3). This shows how the hydration level near the surface of the SC increased due to occlusion (x=0 to 5 µm). Also, the total area under the curve from the surface to the bottom of the SC has increased from 697 to 764, an increase of approximately 10%.

EXAMPLE 2

Effect of Moisturing Products

In this study, two commercial moisturizing treatments ('a'—Olay® Quench, and 'b'—Jergens® Ultra Healing) were used. After an initial baseline reading via CRS, the products were applied for 2 weeks followed by a 1 week regression period during which no product was applied to the sites examined. Product application was 2 µl cm$^{-2}$, twice daily, over sites on the volar forearms of 15 panelists. Panelists did not use moisturizing products other than those provided by the study organizers on their forearms over the entire course of the study. The baseline profile for skin hydration at the beginning of the study (no products applied) is shown on FIG. 4. As shown, the baseline profile for both sites 'a' and 'b' were identical.

Figure 5:
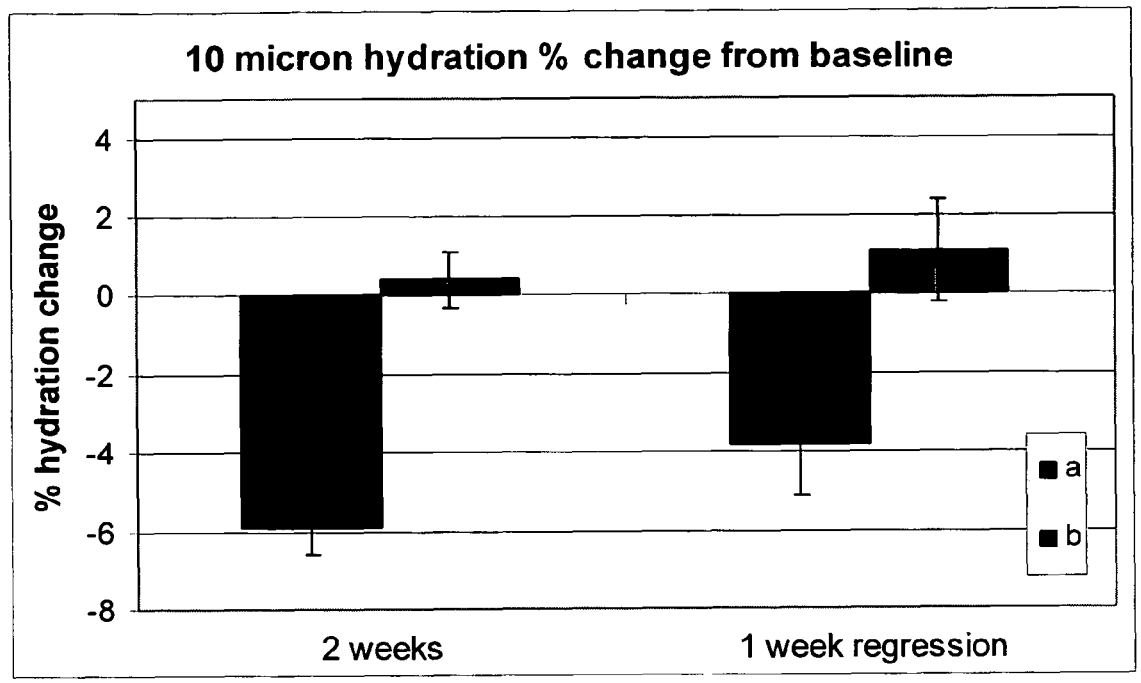
FIG. 5 shows change from baseline in % hydration measured at a fixed depth (10 μm) below the surface of the SC for both treatment regimes ('a' and 'b') during 2 weeks of product application and after 1 week regression.

The change in % hydration for the two moisturizing treatments 'a' and 'b' at the fixed depth of 10 µm data beneath the surface of the SC is given in FIG. 5. Looking at the data in FIG. 5, treatment 'a' appears to be resulting in a dehydration of the SC at 2 weeks usage and after 1 week regression.

Figure 4:
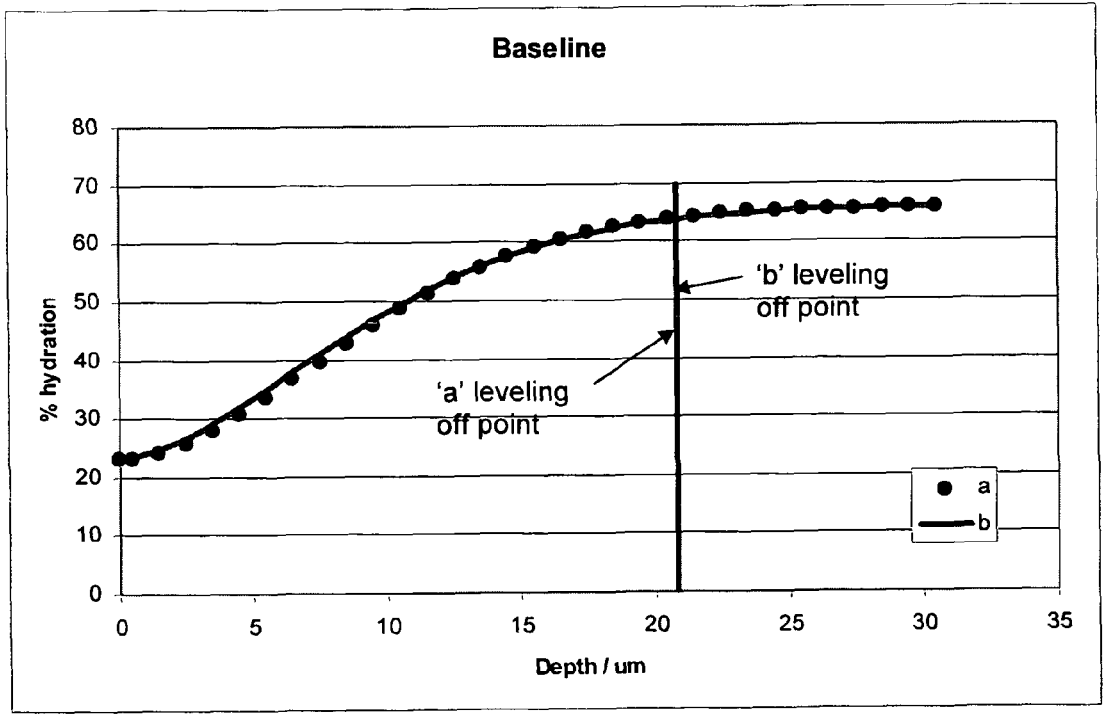
FIG. 4 shows the Raman hydration profiles (averaged across all subjects by treatment) before product application at the start of a study to compare two treatment regimes ('a' and 'b').
Figure 6:
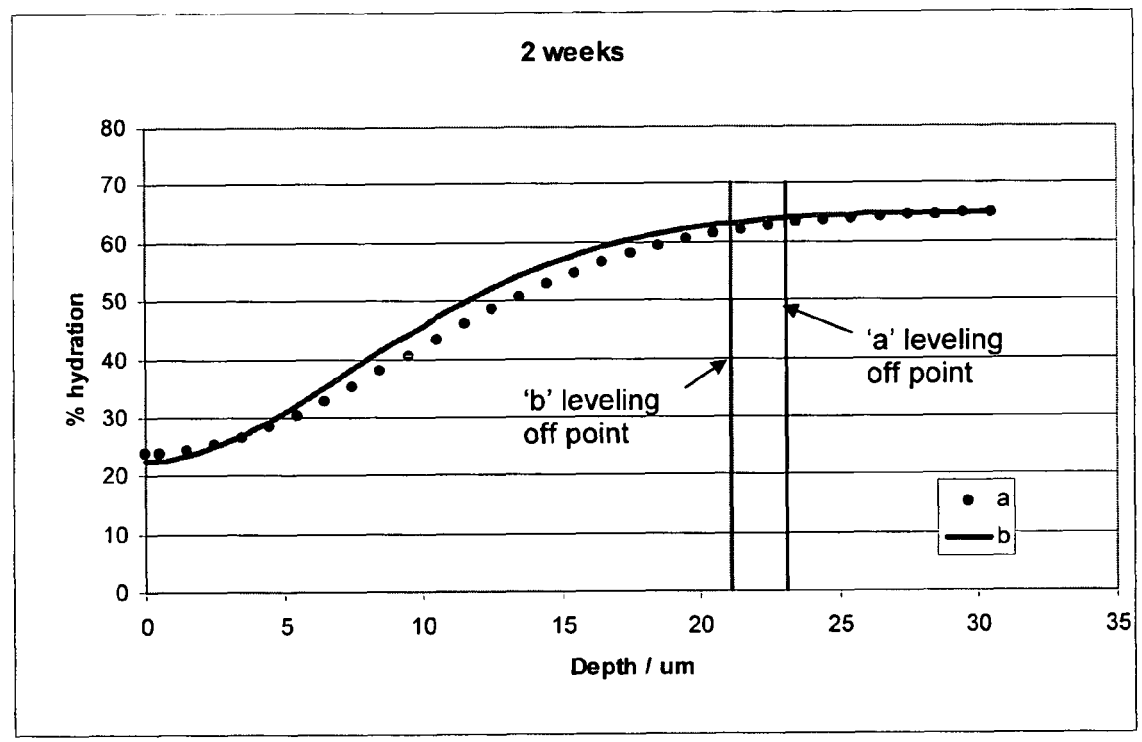
FIG. 6 shows the Raman hydration profiles (averaged across all subjects by treatment) after 2 weeks of product application for the treatment regimes 'a' and 'b'.
Figure 7:
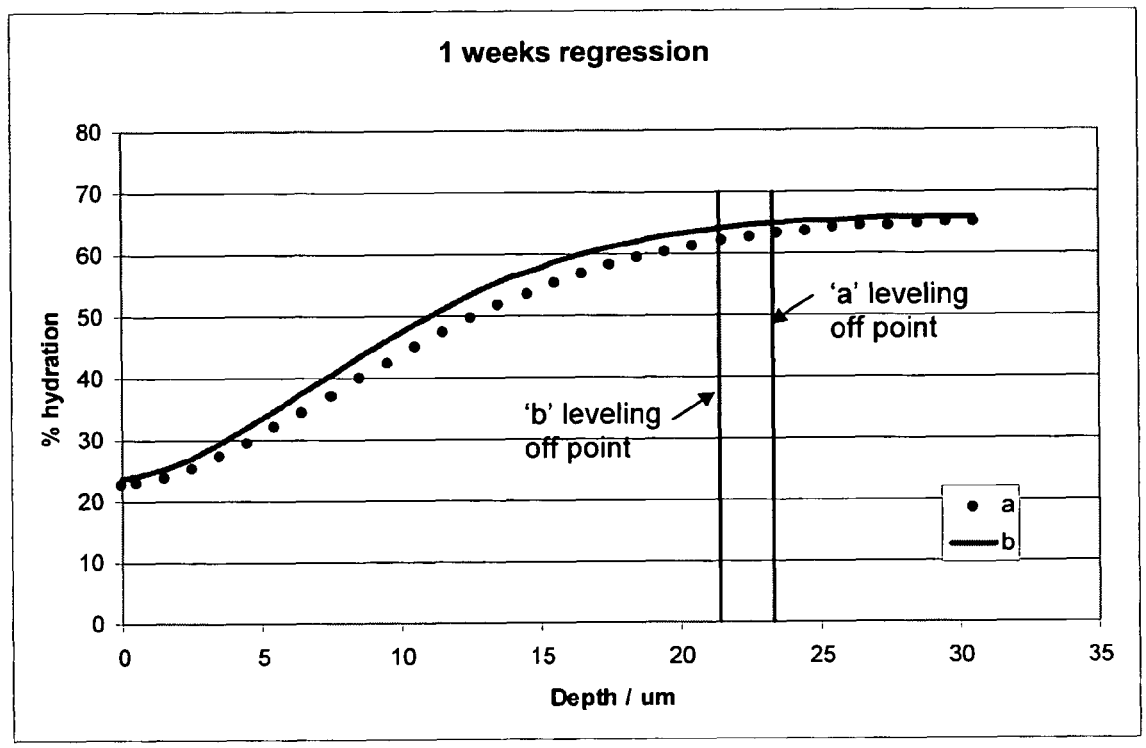
FIG. 7 shows the Raman hydration profiles (averaged across all subjects by treatment) after 1 week regression for the treatment regimes.

However if the shape of the profile at each of these time points is examined, there is a clear difference for treatment 'a' after 2 weeks usage and 1 week regression. FIGS. 6 and 7 show a change in the skin thickness as the leveling off points for treatment 'a' and 'b' are different (where as, at the start of the study—the baseline reading, FIG. 4, shows that the skin at all the sites is equivalent as the leveling off points are coincident). Therefore, measurement only of % hydration at a single depth beneath the surface of the SC is misleading, as treatment 'a' would have appeared to have lowered in % hydration at a fixed depth.

Figure 8:
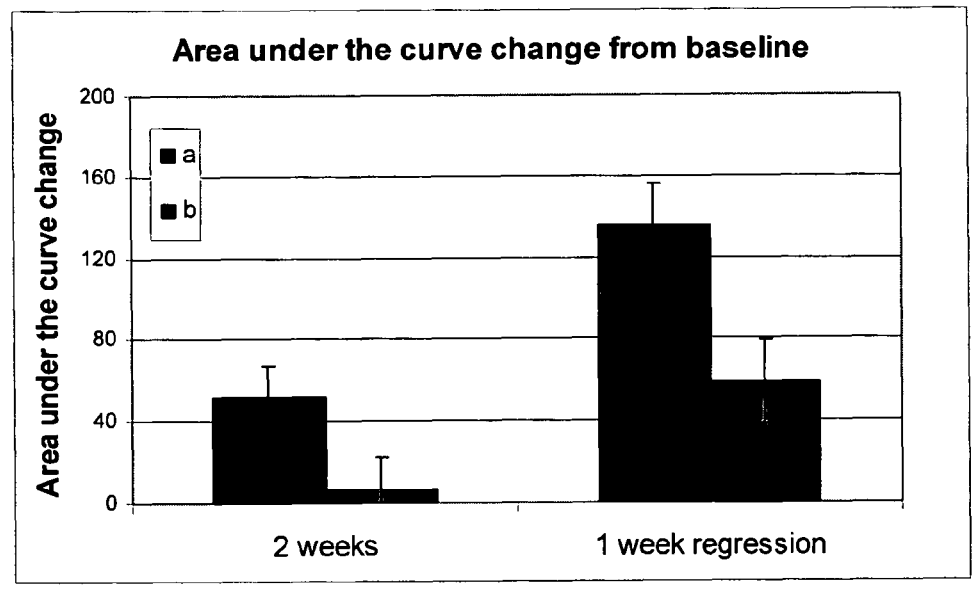
FIG. 8 shows the change from baseline in total area under the curve from the surface of the SC to the leveling off point (determined from the Raman profile) during 2 weeks of product application and 1 week regression for 2 treatment regimes.

Use of the total area under the curve is calculated by taking into account the leveling off point via CRS, (e.g. total hydration level within the SC is shown in FIG. 8). This shows a clear and statistically valid ($p<0.05$) increase in the total hydration within the skin (e.g. total hydration content within the SC) for treatment 'a' which was not observed by examining the % hydration at a fixed depth (the change shown corresponds to approximately a 10% increase in area under the curve for product 'a'). One skilled in statistics may recognize that "p" is a statistical term referring to the probability of the data being real, or having happened by chance. A "p" value of less than 0.05 means that there is a 95% chance that the data is real, and has not happened by chance. All the data generated for this study were analyzed using a gradient threshold of 0.5, as that value has been determined to be most representative of the leveling off point for the experiment.

Examples of potential advertising claims that may result from experiments discussed herein include, but are not limited to: "Increases the water holding capacity of your skin by X% after 2 weeks." This claim would be appropriate when the area under the curve has increased by X% from before treatment to after treatment. Another example of a potential advertising claim would be "Delivers 'ingredient X' to where it is needed in the skin." This claim is related to measurements looking at the location of a specific actives or skin care ingredients within the SC.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All documents cited in the Background, Summary of the Invention, and Detailed Description of the Invention are, in relevant part, incorporated herein by reference; the citation of any document is not to be construed as an admission that it is prior art with respect to the present invention.

What is claimed is:
1. A business method for generating advertising claims, the method comprising the steps of:
(a) determining the before use thickness of the Stratum Corneum on an area of a test subject's skin comprising the steps of:
i. measuring the concentration profile of a Raman-active material as a function of depth within the test area using Confocal Raman Spectroscopy; then ii. processing the Confocal Raman Spectroscopy data obtained to determine said before use thickness of the Stratum Corneum;
(b) providing said test subject with a personal care composition and instructions for use of said personal care composition;
(c) determining the after use thickness of the Stratum Corneum on an area of a test subject's skin after the use of said personal care composition comprising the steps of:
i. measuring the concentration profile of a Raman-active material as a function of depth within the test area using Confocal Raman Spectroscopy; then
ii. processing the Confocal Raman Spectroscopy data obtained to determine said after use thickness of the Stratum Corneum;
(d) calculating, using a computer, the effectiveness of the skin care composition wherein the thickness of the Stratum Corneum before and after the application of the personal care composition are input as parameters when calculating the effectiveness of the personal care composition;
(e) utilizing said effectiveness of the personal care composition to generate said advertising claims.

2. The business method of claim 1 wherein said method is utilized in a store.

3. The business method of claim 1 wherein said method is utilized in a doctor's office.

4. The business method of claim 1 wherein said before use thickness and said after use thickness are processed using the Weibull type algorithm.

5. The business method of claim 1 wherein said method is determined in vivo.

6. The business method of claim 1 wherein said Raman-active material is water.

7. The business method of claim 1 wherein said personal care composition is a skin care composition.

8. The business method of claim 7 wherein said skin care composition comprises at least one moisturizing agent.

9. A business method for generating advertising claims by determining the effectiveness of a skin care composition, the method comprising the steps of:
(i) selecting a Raman-active material linked to the effectiveness of said skin care composition to be determined;
(ii) measuring the before use concentration profile of said Raman-active material as a function of depth within a test area of skin using Confocal Raman Spectroscopy;
(iii) determining the before use thickness of the Stratum Corneum within said test area;
(iv) applying said skin care composition to said test area;
(v) measuring the after use concentration profile of said Raman-active material as a function of depth within said test area using said Confocal Raman Spectroscopy;
(vi) determining said after use thickness of said Stratum Corneum within said test area;
(vii) calculating said effectiveness of said skin care composition as a function of:
a. said before use concentration profile and said after use concentration profile of said Raman-active material; and
b. said before use thickness and said after use thickness of said Stratum Corneum;
(viii) utilizing said before use concentration profile and after use concentration profile and said before use thickness and said after use thickness to generate said advertising claims.

10. A business method of claim 9 wherein said method is determined in vivo.

11. A business method of claim 9 wherein said skin care composition comprises at least one moisturizing agent, and said Raman-active material is water.

12. A business method of claim 9 wherein said effectiveness of said skin care composition is calculated by selecting a specific relative depth of said Stratum Corneum and comparing the amount of said Raman-active material linked to the effect to be determined present at said relative depth before use and after use of said skin care composition.

13. A business method of claim 12 wherein said relative depth of the Stratum Corneum is half-way.

14. A business method of claim 9 wherein said effectiveness of said skin care composition is calculated by summing the amounts of said Raman-active material over the entire depth of said Stratum Corneum before use and after use of said skin care composition and comparing said amounts.

\* \* \* \* \*